United States Patent [19]

Kassis et al.

[11] Patent Number: 4,851,520
[45] Date of Patent: Jul. 25, 1989

[54] METHOD OF MAKING RADIOIODINATED PYRIMIDINE NUCLEOSIDE OR NUCLEOTIDE

[75] Inventors: Amin I. Kassis, Chestnut Hill; Janina Baranowska-Kortylewicz, Boston, both of Mass.

[73] Assignee: President & Fellows of Harvard College, Cambridge, Mass.

[21] Appl. No.: 150,133

[22] Filed: Jan. 29, 1988

[51] Int. Cl.[4] ................. C07H 19/067; C07H 19/073; C07H 19/10
[52] U.S. Cl. .......................................... 536/29; 536/23
[58] Field of Search .................................... 536/23, 29

[56] References Cited

PUBLICATIONS

Keough et al., J. Labelled Compd. Radiopharm., vol. 14, pp. 83-90 (1978).
Bakker et al., Int. J. Appl. Radiat. Isot., vol. 32, pp. 176-178 (1981).
Bergstrom et al., J. Carbohyr., Nucleosides, Nucleotides, vol. 4, pp. 257-269 (1977).

*Primary Examiner*—Ronald W. Griffin
*Assistant Examiner*—Jenny Tou

[57] ABSTRACT

The method of making radioiodinated pyrimidine nucleoside or nucleotide which comprises contacting a water-insoluble halomercuri pyrimidine nucleoside or nucleotide with an aqueous medium containing a dissolved radioactive iodide ion and an oxidizing agent, the molar amounts of said nucleoside or nucleotide and said oxidizing agent being in excess of the molar amount of said iodide, whereby water-soluble radioactive iodinated pyrimidine nucleoside or nucleotide is formed in solution, and separating residual water-insoluble halomercuri pyrimidine nucleoside or nucleotide from said solution.

4 Claims, No Drawings

METHOD OF MAKING RADIOIODINATED PYRIMIDINE NUCLEOSIDE OR NUCLEOTIDE

This invention relates to a method of making radioiodinated pyrimidine nucleosides and nucleotides and pertains more specifically to a heterogeneous phase reaction for making the desired compounds in a form which is readily purifiable, for example by a simple HPLC procedure.

Radioiodinated pyrimidine nucleosides such as 5-iodo-2'-deoxyuridine have been used for many years to label the DNA of proliferating cells in studies of tumor transplantation and of DNA structure among other uses. Radioiodination methods for making such compounds have included electrophilic substitution of hydrogen in the pyrimidine ring by reacting water-soluble pyrimidine nucleosides in aqueous solution with sodium iodide and nitric acid as described by Keough et al., J.Labelled Compd. Radiopharm., Vol. 14, pp. 83–90 (1978) and with sodium iodide and chloramine-T as described by Bakker et al., Int. J. Appl. Radiat. Isot., Vol. 32, pp. 176–178 (1981). Although the radiochemical yields in these processes are high, and satisfactory separation of the product from residual sodium iodide can usually be achieved by chromatography, complete removal of unreacted pyrimidine nucleoside is very difficult because of the more than 20,000-fold excess of this starting material used in the synthesis and requires complicated and lengthy procedures.

There has now been discovered a facile procedure for the preparation of radioiodinated pyrimidine nucleosides and nucleotides which comprises contacting a water-insoluble halomercuri-pyrimidine nucleoside or nucleotide with an aqueous medium containing a dissolved radioactive iodide ion and an oxidizing agent, the molar amount of said nucleoside or nucleotide being in excess of the molar amount of said iodide, whereby water-soluble radioactive iodinated pyrimidine nucleoside or nucleotide is formed in solution, and separating residual water-insoluble halomercuri-pyrimidine nucleoside or nucleotide from said solution. The separation can readily be carried out by conventional filtration procedures. The method is suitable for no-carrier-added syntheses and, following the separation step, requires only a minimal purification process, for example, by conventional HPLC procedures, to produce a product of extremely high purity.

The process of the present invention can be applied to any water-insoluble halomercuri-pyrimidine nucleoside such as 5-chloromercuri cytidine, 5-chloromercuri-2'-deoxycytidine, 5-chloromercuri uridine, 5-chloromercuri-2'-deoxyuridine, or water-insoluble halomercuri-pyrimidine nucleotide such as 5-chloromercuri-cytidine-5'-mono-, di, or tri-phosphate, 5-chloromercuri-2'-deoxycytidine-5'-mono-, di-, or tri-phosphate, 5-chloromercuri-uridine-5'-mono-, di-, or tri-phosphate, or 5-chloromercuri-2'-deoxyuridine-5'-mono-, di-, or tri-phosphate; the corresponding 5-fluoromercuri compounds, and the like may also be used. The water-insoluble nucleosides and nucleotides can be made by well-known procedures as described, for example, in Bergstrom et al., J. Carbohyr., Nucleosides, Nucleotides, Vol. 4, pp. 257–269 (1977).

The radioactive iodide ion may be employed in the form of any water-soluble salt, e.g. an alkali metal salt such as the sodium salt of $^{123}I$, $^{125}I$, $^{131}I$, preferably in carrier-free form.

The oxidizing agent used may be either water-soluble as in the case of Chloramine-T or nitric acid; or it may be water-insoluble as in the case of Iodogen (1,3,4,6-tetrachloro-3α, 6α-diphenylglycoluril).

Both the halomercuri-pyrimidine nucleoside or nucleotide and the oxidizing agent must be employed in molar excess with respect to the iodide ion. Water-insoluble oxidizing agents are preferred because the excess agent is removed from the aqueous medium after reaction completion in the same filtration step by which the excess halomercuri-pyrimidine nucleoside or nucleotide is removed, thus simplifying still more the subsequent high performance liquid chromatography separation used to remove the small amounts of water-soluble by-products present. The amount of excess of these reagents is not critical, but it is usually convenient and desirable to employ at least 1800 molar excess of each, with respect to iodide ion. Larger excesses are limited only by economics and convenience.

The concentration of iodide ion in the aqueous reaction medium is not critical and it may range from 0.1 mCi/mL to 100 mCi/mL, preferably from 0.1 mCi/mL to 10 mCi/mL.

The reaction may be carried out at temperatures up to 100° C. but optimum results are obtained at 20°–30° C. for 1 to 3 hours. Longer or shorter times may be employed at different temperatures and/or iodide concentrations if desired.

After filtration of the reaction mixture to remove excess halomercuri-pyrimidine nucleoside or nucleotide and excess oxidizing agent (when a water-insoluble oxidizing agent is used), the reaction mixture is subjected to high performance liquid chromatography preferably on a reverse phase column (Bonda Pak $C_{18}$) using methyl alcohol/distilled water 20/80 as eluant. Eluates can be assayed by ultraviolet absorption and by gamma ray detection.

The following specific examples are intended to illustrate more fully the nature of the invention without acting as a limitation upon its scope.

EXAMPLE 1

Preparation of 5-chloromercuri-2'-deoxyuridine

2'-Deoxyuridine (0.50 g, 2.20 mmol) was dissolved in 2 mL water and the solution was heated to 50° C. To this solution mercuric acetate (0.74 g, 2.32 mmol) in 3 mL water was added. The mixture was brought to 50° C. and an additional 1 mL water was added. The reaction was allowed to proceed for 2.5 h at 50° C. resulting in a thick white suspension. The heating bath was removed and the mixture cooled to about 40° C. Sodium chloride (0.32 g, 5.45 mmol) in 1 mL water was added to the reaction mixture, and it was stirred for 1 hour. The suspension was filtered, and the white precipitate was washed successively with 0.5 mL 0.1 M NaCl, 0.5 mL water, 0.5 mL 95% ethanol and 0.5 mL diethyl ether. The precipitate was dried in vacuo at about 60° C. for 24 hours giving 0.59 g (57.7%) 5-chloromercuri-2'-deoxyuridine: mp. 210°–211° C. with decomposition (lit. mp. 210.5°–211° C.; Bergstrom, 1977); 'Hnmr (1 M NaCN/$D_2O$) 2.35 ppm. (2H, m, C2'$H_2$), 3.85 ppm. (2H, m, C5'$H_2$), 4.01 ppm. (1H, m, C3'H), 4.46 ppm. (1H, m, C4'H), 6.33 ppm. (1H, t, Cl'H), 7.72 ppm. (1H, s, C6H).

EXAMPLE 2

Preparation of 5-fluoromercuri-2'-deoxyuridine

2'-Deoxyuridine (0.50 g, 2.20 mmol) was reacted with mercuric acetate (.74 g, 2.32 mmol) as described in Example 1 above. Sodium fluoride (0.23 g, 5.45 mmol) in 1 mL water was added after the reaction mixture had cooled to about 40° C. The suspension was stirred for 1 hour and filtered. The precipitate was washed successively with 1 mL 0.1 M sodium fluoride, 1 mL water, 0.5 mL 95% ethanol and 0.5 mL diethyl ether. Drying in vacuo at 60° C. gave 0.48 g (49.1%) 5-fluoromercuri-2'-deoxyuridine: mp. 250°-257° C. with decomposition; 'Hnmr (1 M NaCN/$D_2O$) 2.38 ppm. (2H, t, C2'$H_2$), 3.84 ppm. (2H, m, C5'$H_2$), 4.00 ppm. (1H, m, C3'H), 4.47 ppm. (1H, m, C4'H), 6.35 ppm. (1H, t, Cl'H), 7.51 ppm (1H, s, C6H).

EXAMPLE 3

Preparation of 5-iodo-2'-deoxyuridine (IUdR)

Iodogen (10 mg, 23.1 μmol) and freshly prepared 5-chloromercuri-2'-deoxyuridine (10 mg, 21.6 μmol) were suspended in 0.4 mL water. To this mixture a solution of sodium iodide (3 mg, 20 μmol) in 0.4 mL water was added. The mixture was allowed to react at room temperature for 24 hours during which time it was vigorously stirred. Filtration of the mixture through a 0.22 m Millex filter gave 0.78 mL of clear solution. This was chromatographed by HPLC giving 2.9 mg (41%) IUdR with a retention time ($R_T$) of 7.1 min (identical to an authentic sample). The HPLC revealed the presence of two other components ($R_T$=2.2 min, 3.31%; $R_T$=16.9 min, 9.95%) (FIG. 1). The first peak was also observed when a solution of pure NaI was injected; the last peak was identified as some oxidized form of iodine generated from NaI in the presence of Iodogen, presumably ICl). This latter peak was not observed during the no-carrier-added radioiodination. The synthesis was repeated several times varying the reaction time and the ratio of the reagents. The crude filtrate (prior to HPLC) from one such experiment was analyzed for mercury and 0.2 g/mL was found.

The retention time of Iodogen was established as follows: a saturated solution of Iodogen in methanol was prepared and chromatographed (15 minutes isocratic $H_2O$/$CH_3OH$, 80/20 by volume, followed by a linear gradient to 100% methanol in 10 min); $R_T$ of Iodogen =29 minutes. Sodium iodide was added to the saturated solution of Iodogen, and the mixture was allowed to react for 3 hours after which it was quenched with $Na_2S_2O_5$. The filtrate was chromatographed as described for Iodogen; $R_T$ of the by-product =3.2 minutes.

EXAMPLE 4

Preparation of 5-[$^{125}$I]iodo-2'-deoxyuridine ([$^{125}$I]IUdR)

To the dry mixture of freshly prepared 5-chloromercuri-2'-deoxyuridine (4 mg, 8.6 μmol) and Iodogen (4 mg, 9.3 μmol) was added 1.4 mCi sodium [$^{125}$I]iodide in 0.3 mL water. The mixture was stirred in a closed 2-mL reaction vial at room temperature for 2 hours. The suspension was withdrawn from the reaction vessel into a 5-mL syringe and filtered through a 0.22 μm Millex filter. The reaction vial and filter were washed 4 times with 0.2 mL water. The combined filtrates were injected into the HPLC, and the radioactive content of each fraction determined. Fractions from the peak with an $R_T$ =7.1 minutes, corresponding to that of an authentic sample, afforded 5-[$^{125}$I]iodo-2'-deoxyuridine in 57.1% radiochemical yield (0.8 mCi). The radiochemical purity of the crude [$^{125}$I]IUdR in the filtrate was 99.1%, sodium [$^{125}$I]iodide accounted for the remaining 0.9% of the radioactivity ($R_T$ =2.2 minutes).

There is shown in Table 1 below a summary of yield and purity of [$^{125}$I]IUdR obtained by varying the conditions of the foregoing example.

TABLE 1

Summary of Yields and Purity of [$^{125}$I]IUdR Obtained Under Different Reaction Conditions

| Solvent | Reaction time (h) | ClHgUdR:Iodogen[a] | Percent purity | Percent yield |
|---|---|---|---|---|
| water | 1 | 3:3 | 77.0 | 22.4 |
| water | 3 | 10:2.5 | 97.8 | 36.7 |
| water | 1 | 10:10 | 84.0 | 44.0 |
| water | 2[c] | 10:10 | 99.1 ± 0.4 | 54.8 ± 1.6 |

[a]mg/mL:mg/mL
[c]four runs

EXAMPLE 5

Preparation of 5-[$^{125}$I]iodo-2'-deoxyuridine ([$^{125}$I]IUdR)

The radioiodination of 5-fluoro-2'-deoxyuridine was conducted by substituting 8.6 μmol of it for the 5-chloromercuri-2'-deoxyuridine of Example 4. Approximately 100% of the radioactivity was recovered in the filtrate; the yield of [$^{125}$I]IUdR was about 50% and the remainder of the radioactivity was recovered in the sodium iodide fraction.

EXAMPLE 6

Preparation of 5-[$^{123}$I]iodo-2'-deoxyuridine ([$^{123}$I]IUdR)

To a dry mixture of 5-chloromecuri-2'-deoxyuridine (4 mg, 8.6 mol) and Iodogen (4 mg, 9.3 mol) was added 2.1 mCi sodium [$^{123}$I]iodide in 0.3 mL water. The pH of the sodium iodide solution was adjusted to about 7 using 0.1 M acetic acid. The mixture was stirred in a closed 2-mL reaction vial at room temperature for 3 hours. The suspension was withdrawn from the reaction vessel into a 5-mL syringe and filtered through a 0.22 m Millex filter. The reaction vial and the filter were washed 4 times with 0.2 mL water. The combined filtrates were injected into the HPLC, and the fraction were collected and counted in a dose calibrator. The radioactive fractions which corresponded to an authentic sample ($R_T$ =7.1 minutes) afforded 5-[$^{125}$I]iodo-2'-deoxyuridine in 65.7% radiochemical yield (1.37 mCi). The radiochemical purity of the crude [$^{123}$I]IUdR in the filtrate was 98%. Sodium [$^{123}$I]iodide accounted for 1.2 % of the radioactivity ($R_T$=2.2 minutes), and the remaining 0.8% was associated with unidentified species with $R_T$=4.1 minutes.

Similar results can be obtained when other water-insoluble halomercuri pyrimidine nucleosides or nucleotides are employed.

What is claimed is:

1. The method of making radioiodinated pyrimidine nucleoside or nucleotide which comprises contacting a water-insoluble halomercuri pyrimidine nucleoside or nucleotide with an aqueous medium containing a dissolved radioactive iodide ion and iodogen, the molar amounts of said nucleoside or nucleotide and said iodogen being in excess of the molar amount of said iodide, whereby water-soluble radioactive iodinated pyrimidine nucleoside or nucleotide is formed in solution, and separating residual water-insoluble material including halomercuri pyrimidine nucleoside or nucleotide from said solution.

2. The method as claimed in claim 1 in which said insoluble nucleoside or nucleotide is 5-chloromercuri pyrimidine nucleoside or nucleotide.

3. The method as claimed in claim 2 in which said insoluble nucleoside is 5-chloromercuri-2'-deoxyuridine.

4. The method as claimed in claim 1 in which said insoluble nucleoside or nucleotide is fluoromercuri pyrimidine nucleoside or nucleotide.

* * * * *